United States Patent [19]

Bell et al.

[11] Patent Number: 4,600,175
[45] Date of Patent: Jul. 15, 1986

[54] REFRACTING INSTRUMENT SUPPORT ARM

[75] Inventors: Charles D. Bell, Mickleton, N.J.; Pat Smith, Berwyn, Pa.

[73] Assignee: Charles D. Bell Incorporated, Westville, N.J.

[21] Appl. No.: 662,267

[22] Filed: Oct. 18, 1984

[51] Int. Cl.⁴ .............................................. A47G 29/00
[52] U.S. Cl. ..................... 248/122; 248/298
[58] Field of Search ............... 248/122, 287, 295.1, 248/298, 124, 125; 179/147

[56] References Cited

U.S. PATENT DOCUMENTS

| | | | |
|---|---|---|---|
| 1,795,296 | 3/1931 | DeZeng | 248/124 X |
| 1,868,304 | 7/1932 | Cargill | 248/298 X |
| 2,291,999 | 8/1942 | Wilson et al. | 248/124 |
| 2,408,247 | 9/1946 | Wekeman | 248/122 |
| 4,116,512 | 9/1978 | Wiser | 292/251.5 X |
| 4,234,155 | 11/1980 | Destree | 248/124 X |

Primary Examiner—J. Franklin Foss
Assistant Examiner—David L. Talbott
Attorney, Agent, or Firm—Duffield & Lehrer

[57] ABSTRACT

A support for an ophthalmic refracting instrument includes a vertical support column preferably comprised of a pair of closely spaced upright members. A rigid horizontal support member has one end secured to the top of the vertical support column. The free end of the support member extends to the vicinity above and in front of the patient's chair. The support member includes an elongated horizontally extending bar therein. The refracting instrument is mounted on a bar carried by a slide assembly. The slide assembly includes a pair of bearing blocks which surround the elongated shaft so that the entire slide assembly along with the refracting instrument can be slid between an inoperative position where it is adjacent the vertical support column and an operative position where the refracting instrument is in front of the patient. Magnets act as stop mechanisms and hold the slide assembly in each of its two extreme positions.

5 Claims, 5 Drawing Figures

REFRACTING INSTRUMENT SUPPORT ARM

BACKGROUND OF THE INVENTION

The present invention is directed toward a support for a refracting instrument and more particularly toward a support arm which allows an ophthalmic refracting instrument to be slid between a remote inoperative position and an operative position wherein it is positioned in front of a patient.

Refracting instruments are used by ophthalmologists, optometrists and other eye care specialists to help determine the condition of a patient's eyes and eyesight and assist the doctor in determining the amount and nature of corrections that need be made. One such refracting instrument commonly used is known as the Phoroptor manufactured by American Optical Corporation of Southbridge, Mass.

Conventionally, refracting instruments are mounted at the end of a horizontally disposed refracting arm which, in turn, is pivotally mounted to a vertical pole which is positioned to the side of the patient's chair. The refracting instrument is brought into the operative position where it is directly in front of the patient's eyes by the doctor reaching out to his side where the instrument is in its inoperative position and swinging the refracting instrument and the support arm in a circular arc around the pole until the refracting instrument is in its proper position. After the refracting instrument has been utilized, the doctor then reverses this procedure and swings the instrument and support arm back through the circular arc around the pole to the inoperative position.

While these conventional support arms have been somewhat useful, they do have several disadvantages. They require a great deal of space since they are moved in an arcuate direction. Thus, no other instruments or furniture or the like can be located in the path of movement of the refracting instrument and support arm. Furthermore, the inoperative position into which the refracting instrument is moved very often cannot be reached by the doctor when he is sitting in his chair opposite the patient. Thus, it is necessary for the doctor to stand up to retrieve the refracting instrument when he desires to use the same. Even further, the refracting instrument is not always easily brought into its proper position in front of the patient. Because of the manner in which it is moved, the instrument is not always parallel to the patient's eyes nor to the chart which is to be viewed by the patient through the refracting instrument.

SUMMARY OF THE INVENTION

The present invention is designed to overcome the deficiencies of the prior art conventional supports discussed above. This is accomplished in accordance with the present invention by providing a support for an ophthalmic refracting instrument which includes a vertical support column preferably comprised of a pair of closely spaced upright members. A rigid horizontal support member has one end secured to the top of the vertical support column. The free end of the support member extends to the vicinity above and in front of the patient's chair. The support member includes an elongated horizontally extending bar therein. The refracting instrument is mounted on a bar carried by a slide assembly. The slide assembly includes a pair of bearing blocks which surround the elongated shaft so that the entire slide assembly along with the refracting instrument can be slid between an inoperative position where it is adjacent the vertical support column and an operative position where the refracting instrument is in front of the patient. Magnets act as stop mechanisms and hold the slide assembly in each of its two extreme positions.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

DETAILED DESCRIPTION OF THE PREFERRED EMBODIMENT

Figure 1:
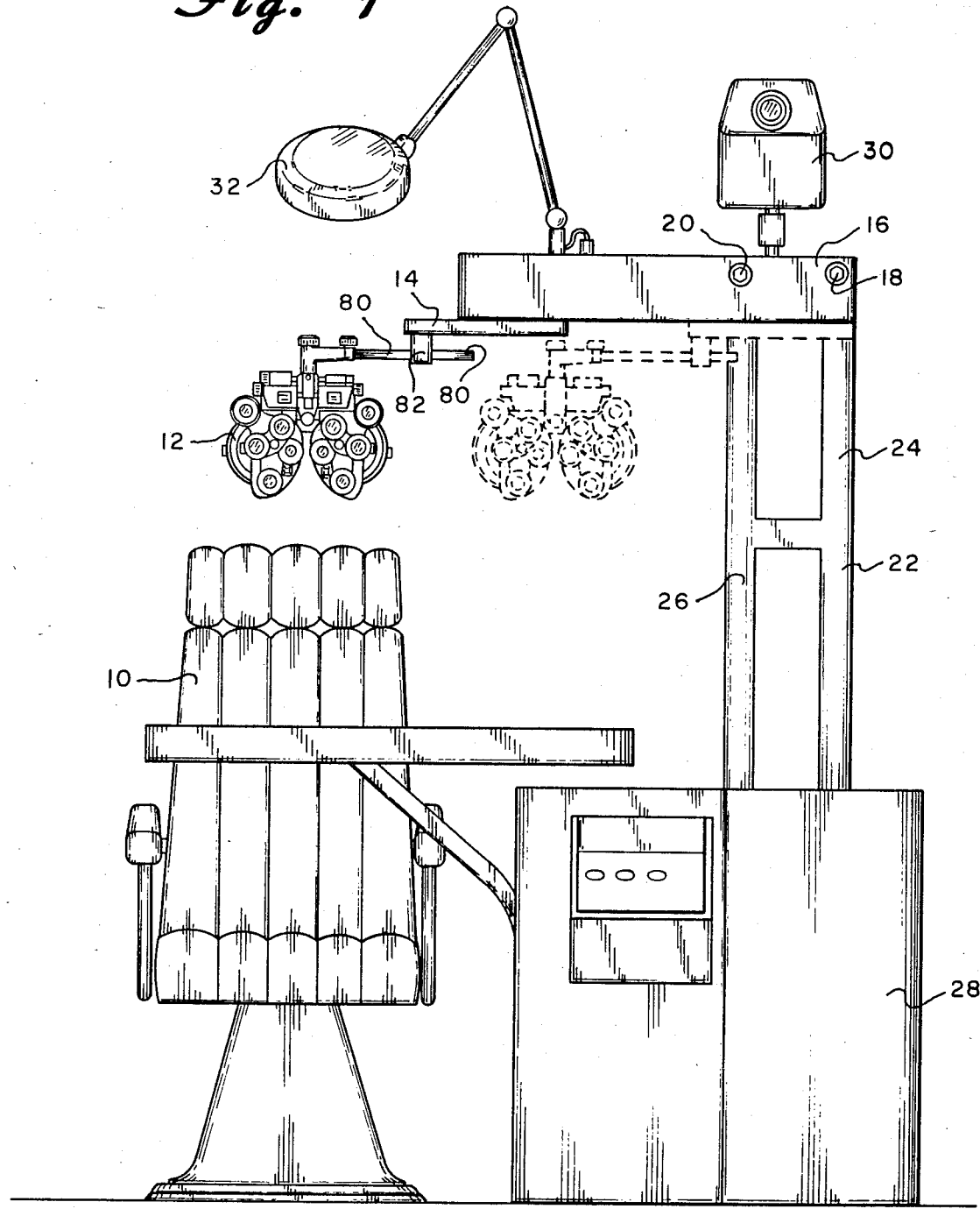
FIG. 1 is a front elevational view of an ophthalmic chair and related equipment illustrating a refracting instrument and a refracting instrument support arm constructed in accordance with the principles of the present invention.

Referring now to the drawings in detail wherein like reference numerals have been used throughout the various figures to designate like elements, there is shown in FIG. 1 an elevational view of a portion of an ophthalmologist's office showing the arrangement of an ophthalmic chair 10 and a refracting instrument 12. In accordance with the present invention, the details of which will be explained hereinafter, the refracting instrument 12 is slideably mounted by way of a slide assembly 14 to a rigid elongated support member 16. The slide assembly 14 is slideably movable between a first position, shown in phantom, wherein the refracting instrument 12 is in an inoperative position toward the right side of the support member 16 as viewed in FIG. 1 and an operative position, shown in solid lines, wherein the refracting instrument 12 is located above and forward of the ophthalmic chair 10 where it would be directly in front of the eyes of a patient sitting in the chair 10.

The support member 16 is secured by way of bolts 18 and 20 to the upper end of a vertical column 22 comprised of upright members 24 and 26. The lower portion of the vertical column 22 is secured to an equipment cabinet 28 or some other similar structure. Because the support member 16 is fixed and rigid, it can be used to support additional periphery equipment such as a chart projector 30 and a lamp 32.

Figure 2:
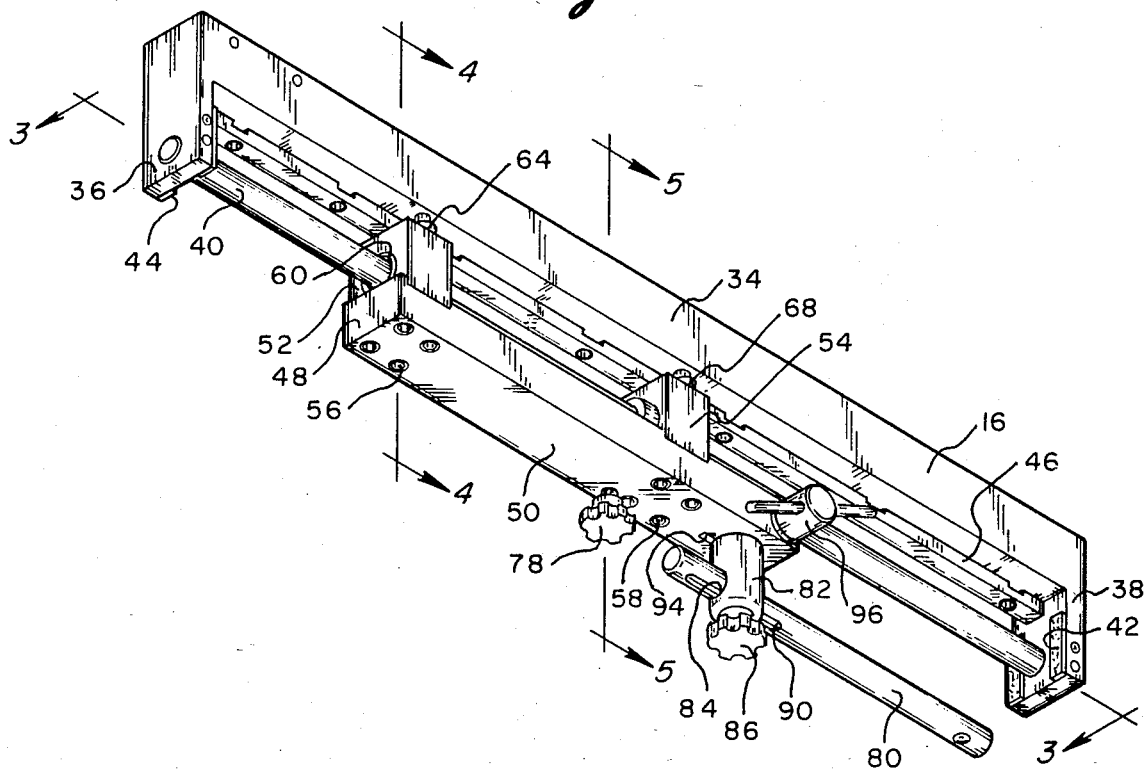
FIG. 2 is a bottom, side perspective view of the support arm with the cover removed so as to show the details thereof.

The details of the actual support arm and slide assembly are shown in FIGS. 2-5. FIG. 2 is a lower perspective view of the same taken from the rear side of FIG. 1 since additional components can be seen from this view. Furthermore, FIG. 1 illustrates the support member and slide assembly with a cover thereon. This cover has been removed in the remaining figures so as to expose some of the features which otherwise would be hidden. Thus, in viewing FIGS. 2-5, it must be kept in mind that the cover of FIG. 1 has been removed and that FIGS. 2 and 3, in particular, are being viewed from the exact opposite direction of FIG. 1.

Referring now to FIGS. 2-5, it can be seen that the elongated support member 16 includes an upper substantially rectangular portion 34 having a pair of downwardly extending ears 36 and 38. Extending between the ears 36 and 38 parallel to but spaced from the rectangular portion 34 is an elongated shaft 40 of substantially circular cross section. Also mounted on the inner faces of the ears 36 and 38 are magnets 42 and 44, the significance of which will be described hereinafter. Also mounted on the support member 16 on the undersurface of the rectangular portion 34 thereof is a narrow track 46. The track 46 rises from the lower wall of the rectangular portion 34 and extends substantially throughout the entire length of the support member 16 parallel to but above the shaft 40.

Located beneath the support member 16 is a slide assembly 48. The slide assembly 48 includes a lower elongated rectangular block 50 and a pair of spaced apart bearing blocks 52 and 54 secured to the upper surface thereof by way of a plurality of screws 56 and 58. The bearing blocks 52 and 54 include axially aligned openings 60 and 62 therein which allow the blocks to slide along the shaft 40 which passes through the openings 60 and 62. While not specifically shown in the figures, it will be understood that suitable ball bearings or the like are provided within the bearing blocks 52 and 54 so as to provide a smooth and substantially frictionless free sliding action between the bearing blocks and the shaft 40. The bearing blocks are also preferably made from a paramagnetic material so as to interact with the magnets 42 and 44. Thus, when the slide assembly 48 is in the inoperative position such as shown in phantom in FIG. 1, it tends to be maintained in that position by the magnetic attraction between the magnets 44 and the bearing block 52. When the slide assembly 48 is brought into the operative position such as shown in solid lines in FIG. 1, it tends to remain in that position as a result of the interaction between the magnets 42 and the bearing block 54.

In order to prevent the slide assembly 48 from rotational movement around the axis of the shaft 40, each of the bearing blocks 52 and 54 is provided with a pair of follower wheels. Wheels 64 and 66 are mounted on the top of block 52 and wheels 68 and 70 are mounted on the top of block 54. As seen most clearly in FIGS. 4 and 5, each of the follower wheels is mounted for rotation about a vertical axis and each pair has one wheel lying on either side of the track 46. As the slide assembly 48 moves axially along the shaft 40, the wheels 64, 66, 68 and 70 engage the track 46 and maintain the slide assembly 48 in its angular position shown in FIGS. 4 and 5 by preventing rotation about the axis of the shaft 40.

While the magnets 42 and 44 will normally be all that is necessary to maintain the slide assembly 48 in the operative or inoperative position, there may be occasions when it is necessary to provide a more positive lock. For example, a hyperactive patient being examined with the use of a refracting instrument may have a tendency to move his head with sufficient force to also displace the slide assembly against the force of the magnet 42. Thus, the slide assembly 48 is also provided with a positive locking means comprised of a split ring element 72 which surround the shaft 40. An elongated screw member 74 engages the internal threads adjacent the split portion of the ring 72 and extends downwardly through bore 76 in the rectangular block 50 to terminate in a handle 78. It should be readily apparent to those skilled in the art that the slide assembly 48 can be locked in any axial position along the shaft 50 by turning the handle 78 in the proper direction to draw the split ends of the rings 72 together to thereby clamp the same around the shaft 40. The lock is released by turning the handle or knob 78 in the opposite direction to again open the ring 72.

Figure 3:
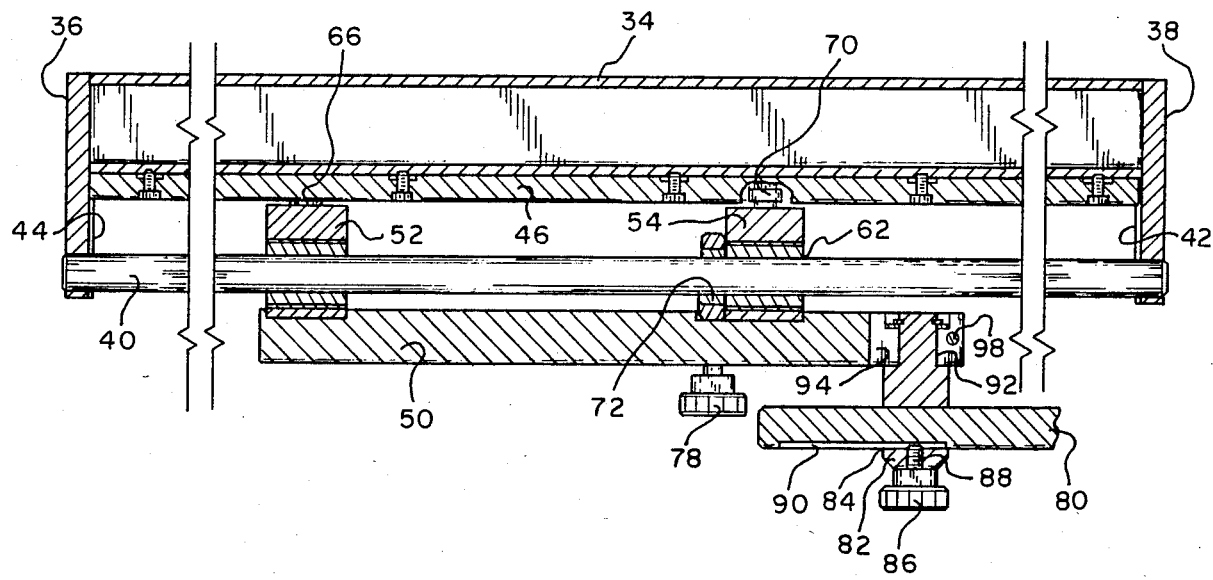
FIG. 3 is a cross-sectional view taken through the line 3—3 of FIG. 2.
Figure 4:
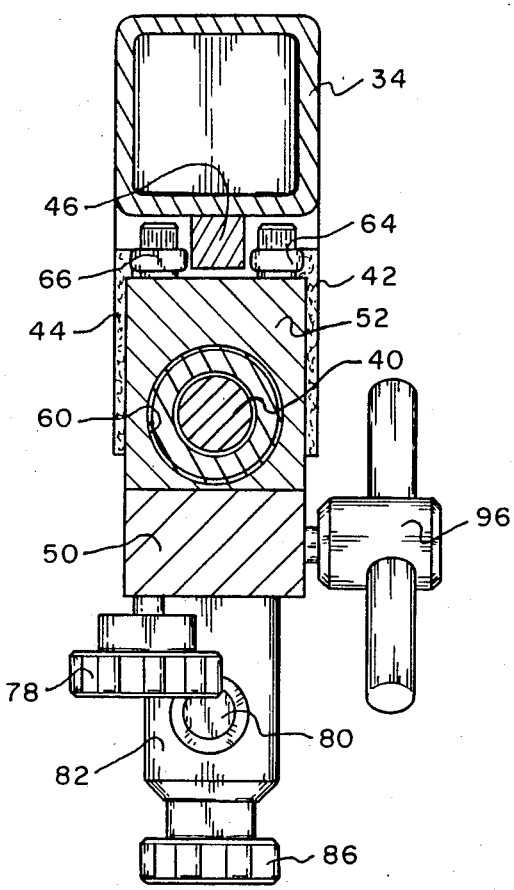
FIG. 4 is a cross-sectional view taken through the line 4—4 of FIG. 2.
Figure 5:
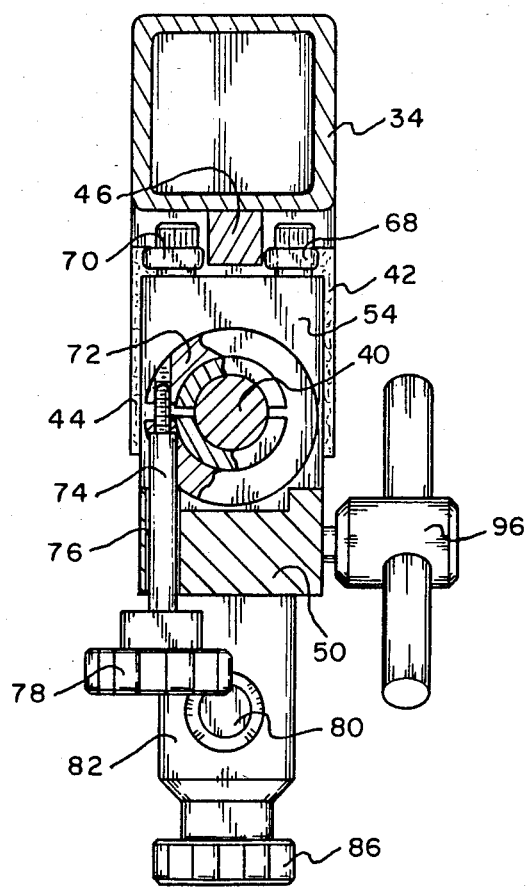
FIG. 5 is a cross-sectional view taken through the line 5—5 of FIG. 2.

As shown most clearly in FIG. 1, the refracting instrument 12 is connected in a known manner to the rigid adjustment bar 80. As shown in FIGS. 2 and 3, the bar 80 is mounted to the slide assembly 48 by way of post 82. Post 82 includes an opening 84 therein which is complementary to the shape of the bar 80. The bar 80 can be slid into and out of the opening 84 until the refracting instrument is in the proper position. Normally, once the refracting instrument is in the proper position, further adjustments would not be necessary. That is, the slide assembly would only have to be initially adjusted when it is first installed in a doctor's office. Once the bar 80 is in its proper position, it is locked therein by turning knob 86 which, in turn, tightens screw 88 against the bar 80 within the groove 90 formed in the bar. The screw 88 entering the groove 90 also prevents rotation of the bar 80 about its own axis.

If desired, the adjustment bar 80 and the refracting instrument 12 can also be rotated about the axis of the post 82. The post 82 is mounted to the rectangular block 50 of the slide assembly 48 through an opening 92 passing vertically therethrough. The end of the block 50 is split as shown at 94 so that the opening 92 can be made smaller or larger by turning the handle 96 which draws the split ends together by use of screw 98. Thus, when it is desired to rotate the adjustment bar 80 and the refracting instrument 12 about the axis of the post 82, handle 96 is loosened and post 82 is turned. When the instrument is in the desired position, handle 96 is tightened. Again, it normally would be necessary to make an adjustment only when the equipment is first installed.

From the foregoing, it can be seen that the present invention is substantially easier and more convenient to use than prior refracting instrument support arms. The instrument 12 can be easily slid from an inoperative position to an operative position by a doctor sitting directly in front of the patient. The doctor need not stand nor reach very far. Furthermore, very little space is required. While there is no means provided for moving the refracting instrument 12 up or down, this is not necessary since substantially all chairs are electrically movable up and down. Thus, if the instrument is not in the proper vertical position, the doctor merely needs to depress a foot switch which will move the chair and therefore the patient either up or down into the proper position.

The present invention may be embodied in other specific forms without departing from the spirit or essential attributes thereof and accordingly, reference should be made to the appended claims rather than to the foregoing specification as indicating the scope of the invention.

We claim:

1. A support for a refracting instrument comprising:
a substantially vertical support column;
a fixed and rigid elongated support member secured to said vertical column adjacent one end of said support member and extending substantially horizontally from said column, said support member including an elongated shaft of substantially circular cross section;

a slide assembly carried by said support member and being slideably mounted thereon, said slide assembly including a pair of spaced apart bearing blocks having substantially circular openings therein which allow said blocks to slide along said shaft with said shaft passing through said openings, said slide assembly being freely slideably movable between a first position adjacent said support column and a second position remote from said column and adjacent the free end of said support member;

means for preventing said slide assembly from rotational movement around the axis of said shaft, said preventing means including an elongated fixed track lying above and extending parallel to said shaft and a pair of wheels carried at the top of said bearing blocks which ride on said track;

means adjacent each end of said support member for maintaining said slide assembly in said first and second positions;

a rigid bar adjustably mounted on said slide assembly and being adapted to carry a refracting instrument thereon.

2. The support as claimed in claim 1 further including means for locking said slide assembly against further movement in substantially any position relative to said support member.

3. The support as claimed in claim 1 wherein said rigid bar is rotatably mounted on said slide assembly.

4. The support as claimed in claim 1 further including a chart projector and a lamp mounted on said support member.

5. The support as claimed in claim 1 wherein said means for maintaining said slide assembly in said first and second positions are magnetic.

* * * * *